United States Patent
Rom

(10) Patent No.: US 7,657,313 B2
(45) Date of Patent: Feb. 2, 2010

(54) ADAPTIVE CARDIAC RESYNCHRONIZATION THERAPY SYSTEM

(75) Inventor: Rami Rom, Zichron Yaacov (IL)

(73) Assignee: Ai-Semi Ltd, Giranot (IL)

( * ) Notice: Subject to any disclaimer, the term of this patent is extended or adjusted under 35 U.S.C. 154(b) by 293 days.

(21) Appl. No.: 10/565,279

(22) PCT Filed: Jul. 20, 2004

(86) PCT No.: PCT/IL2004/000659

§ 371 (c)(1),
(2), (4) Date: Jan. 20, 2006

(87) PCT Pub. No.: WO2005/007075

PCT Pub. Date: Jan. 27, 2005

(65) Prior Publication Data

US 2006/0235477 A1    Oct. 19, 2006

(51) Int. Cl.
*A61N 1/00* (2006.01)
(52) U.S. Cl. ...................................................... 607/17
(58) Field of Classification Search ................ 607/4–28, 607/45
See application file for complete search history.

(56) References Cited

U.S. PATENT DOCUMENTS

| | | | | |
|---|---|---|---|---|
| 5,251,626 A * | 10/1993 | Nickolls et al. | ................ | 607/14 |
| 5,800,467 A * | 9/1998 | Park et al. | ...................... | 607/17 |
| 6,242,988 B1 * | 6/2001 | Sarpeshkar | .................. | 331/111 |
| 6,704,599 B2 * | 3/2004 | Baker | .......................... | 607/14 |
| 7,280,989 B1 * | 10/2007 | Hoppensteadt et al. | ........ | 706/30 |
| 2003/0158587 A1 * | 8/2003 | Esteller et al. | ................. | 607/45 |

* cited by examiner

*Primary Examiner*—Scott M Getzow

(57) ABSTRACT

A system including a learning module and an algorithmic module for learning a physiological aspect of a patient body and regulating the delivery of a physiological agent to the body. An embodiment of the invention is an adaptive CRT device performing biventricular pacing in which the AV delay and VV interval parameters are changed dynamically according to the information supplied by the IEGM, hemodynamic sensor and online processed data, in order to achieve optimal hemodynamic performance.

A learning module, preferably using artificial neural network, performs the adaptive part of the algorithm supervised by an algorithmic deterministic module, internally or externally from the implanted pacemaker or defibrillator.

20 Claims, 9 Drawing Sheets

ADAPTIVE CARDIAC RESYNCHRONIZATION THERAPY SYSTEM

FIELD OF THE INVENTION

The present invention relates generally to medical devices implementing a closed loop processing employing feed back control mechanism. More specifically invention deals with adaptive cardiac pacemaker and ICD devices.

BACKGROUND OF THE INVENTION

Implanted pacemakers and intracardiac cardioverter defibrillators (ICD) deliver therapy to patients suffering from various heart-diseases (Clinical Cardiac Pacing and Defibrillation—$2^{nd}$ edition, Ellenbogen, Kay, Wilkoff, 2000). It is known that the cardiac output depends strongly on the left heart contraction in synchrony with the right heart (see U.S. Pat. No. 6,223,079). Congestive heart failures (CHF) is defined generally as the inability of the heart to deliver enough blood to meet the metabolic demand. Often CHF is caused by electrical conduction defects. The overall result is a reduced blood stroke volume from the left side of the heart. For CHF patients a permanent pacemaker with electrodes in 3 chambers, that are used to re-synchronize the left heart contraction to the right heart is an effective therapy, ("Device Therapy for Congestive Heart Failure", K. Ellenbogen et al, Elsevier Inc. (USA), 2004). The resynchronization task demands exact pacing management of the heart chambers such that the overall stroke volume is maximized for a given heart rate (HR), where it is known that the key point is to bring the left ventricle to contract in synchrony with the right ventricle. Clearly, the re-synchronization task is patient dependent, and with each patient the best combination of pacing time intervals that restores synchrony are changed during the normal daily activities of the patient. For these reasons, next generation cardiac re-synchronization therapy devices should have online adaptive capabilities according to Hemodynamic performance. In a recent publication by D. Odonnell et al titled, "Long-Term Variations in Optimal Programming of Cardiac Resynchronization Devices", PACE 28; January 2005; 24-26, the authors reported the results of a clinical study with 40 CHF patients. The authors found that the optimal atriaventricular (AV) delay and VV interval, obtained using echocardiography, varied significantly during 9 months of patient follow-ups. The authors explained the results by a slow and gradient improvement in the cardiac function due to the implanted CRT devices that generated a reverse remodeling of the left ventricle.

Currently available cardiac resynchronization therapy (CRT) devices have drawbacks that prevent the achievement of an optimally delivered CRT and are listed:—

1. Programming and troubleshooting CRT device—Optimizing the CRT device using echocardiography is expansive, time consuming and operator dependent. The clinician should optimize both the AV delay, in order to achieve maximal diastolic filling time, and the interventricular delay (W interval) in order to achieve resynchronisation of heart chambers contractions.

2. Consistent Delivery of CRT—There are several reasons why CRT is not delivered consistently, and some times is not delivered at all for hours. Examples are failure to optimise the AV delay and low maximal tracking rate.

3. Follow Ups—The clinician must perform the complex task of optimization and programming of the CRT device, first at implantation and then at each follow-up.

4. CRT non-responders, 30% of the patients do not respond to CRT.

AV delay optimization in dual chamber pacemakers and defibrillators are as important clinically as the AV delay optimization of CRT devices. Dual chamber devices use one atrial electrode and one ventricular electrode, and a ventricular pacing occurs after the pre-programmed AV delay measured from a sensed or paced atrial event ends. The AV delay depends on the heart rate and on the stress conditions which vary from patient to patient. Furthermore, the AV delay of a patient varies depending on the daily activities. Therefore a fixed pre-programmed AV delay scheme is less then optimal. Loss of AV synchrony is a major cause for a pacemaker syndrome as quoted in Beyerbach D. M. and Cadman C. Oct. 10, 2002, in http://www.emedicine.com/med/topic2919.htm "Pacemaker Syndrome", the contents of which are incorporated herein by reference. Ellenbogen et al. cited above, focused on clinical utility and proposed that "pacemaker syndrome represents the clinical consequences of AV dyssynchrony or sub-optimal AV synchrony, regardless of the pacing mode."

Artificial neural networks are known for their superior performance in processing in performing tasks as compared to standard algorithmic processing, such as adaptive control and pattern recognition. The spiking neural networks architecture is a unique form of artificial neural networks that are inspired by the biological nerve system. Spiking neurons architectures, applications and learning rules are reviewed by Wolfgang Maass et. al. "Pulsed Neural Network", The MIT Press, London England (2001). Rate responsive heart stimulation device using neural networks has been proposed in U.S. Pat. No. 5,782,885

DETAILED DESCRIPTION OF THE PRESENT INVENTION

General System Architecture

A device of the invention is a feed-back controlled system for delivering input stimuli to the patient's body, in a manner which takes account of the body's significant physiological status relating to the delivered input stimuli.

Figure 1:
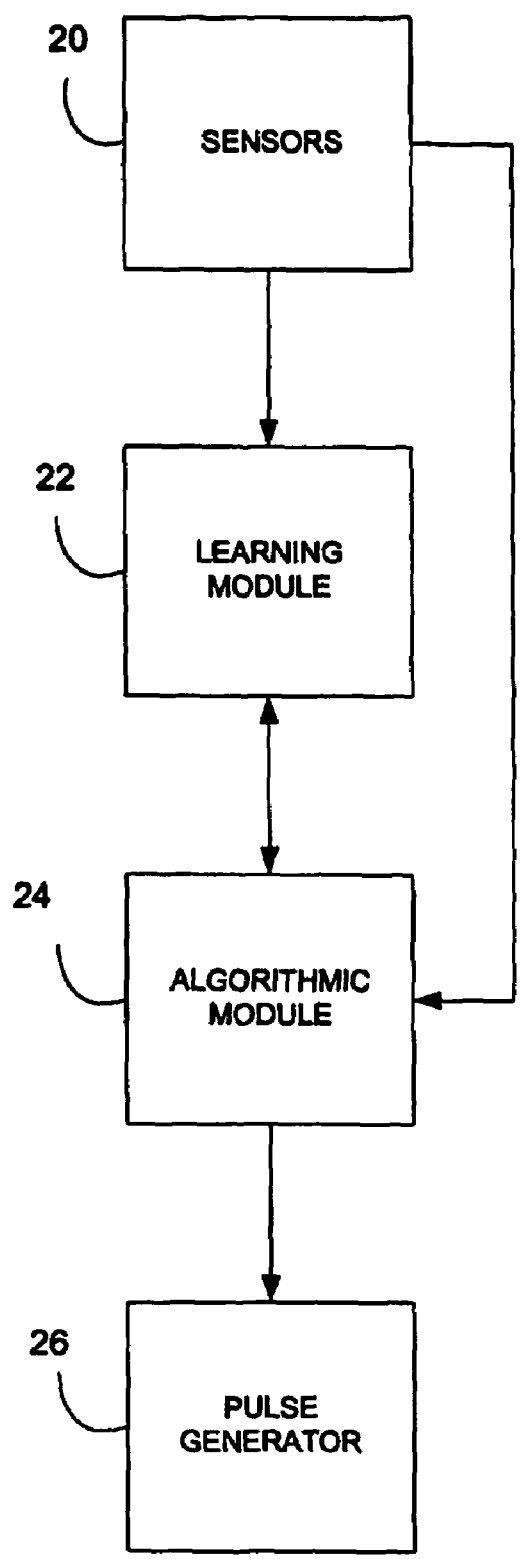
FIG. 1 is a schematic general description of an adaptive CRT system of the present invention.

A system of the invention is an adaptive, hemodynamic sensitive device, for regulating the controlled delivery of physiologically active signals, chemical or electrical. A most typical implementation is the regulation of heart ventricular contractions. In FIG. 1 to which reference is now made, a schematic description of the system of the invention shows its main building blocks. Sensors 20 feed physiological information into a learning module which is typically a neural network module 22 and to the algorithmic module 24. Algorithmic module 24 receives processed data from the neural network module and controls the adaptations schemes of the neural network module 22. Pulse generator 26 issues impulses at time and places as controlled only by algorithmic module 24.

In a preferred embodiment of the invention, the system as described above forms a unitary block implanted in the patient's heart, a cardiac pacemaker or defibrillator, with sensors positioned at critical sites, and pulsing electrodes applied at strategic sites in or about the heart. In other embodiments, only the pacing module is implanted, whereas the neural network module is not implanted in the patient's body, but is communicable through a communications link. Accordingly, the neural network module receives through a typically wireless link, information regarding hemodynamic condition of the patient and the electrical behaviour of the heart.

The main two modules in which the invention is implemented are the algorithmic module and the neural network module. In some embodiments, both modules are implemented in one processor, whereas in other embodiments two different processors are employed, for the algorithmic and for the neural network module, respectively.

Operational Modes of the Adaptive CRT Device

The adaptive CRT device of the invention can operate in either an adaptive or a non-adaptive mode. In accordance with the present invention a clinician programs the AV delay parameter and the VV interval parameter of the pacemaker using an external programmer as with the prior art methods. The initial programmed values are used as safety baseline for the present invention adaptive CRT device Initially, the adaptive CRT device operates in the non-adaptive CRT mode in which the neural network module synaptic weights are trained to predict the programmed values of the AV delay and VV interval using a supervised learning scheme while ignoring the hemodynamic sensor input. When a convergence criterion is met, the master algorithmic module switches to the adaptive CRT mode whereby the AV delay and VV interval are changed dynamically related to the input from hemodynamic sensor. Under the adaptive regime, the neural network module working with the deterministic algorithmic module optimises the AV delay and VV interval continuously promoting optimal hemodynamic performance, which is measurable for example as cardiac output at all heart conditions. Whenever the neural network module fails to find a set of parameters, AV delay and VV interval, that generates a better hemodynamic performance compared to the baseline value obtained with the initial programmed values, or any failure condition that might be detected by the algorithmic master module, the adaptive CRT device switches back to pacing with the programmed fixed values, i.e in the non adaptive CRT mode. Such failure condition might be caused for example by a dislocation of the sensor that generates an in physiological signal pattern. In the non adaptive CRT regime, the adaptive CRT device of the present invention tries again to converge and to switch to the adaptive CRT mode as explained above.

Artificial neural networks are known to have advantages over standard algorithmic processing in performing tasks such as adaptive control and pattern recognition. However, artificial neural networks are not deterministic and may lead to quite unexpected results. In the case of cardiac pacemakers and other life saving medical appliances, the occurrence of results beyond acceptable limits. Thus, a limit setting device, is employed in the embodiments of the present invention for confining the range of parameters provided by the neural network. Typically, artificial neural networks are designed and trained for a specific task. Unsupervised learning network architectures are very limited and are not used in many applications. Applications based on artificial neural networks that use supervised learning are far more successful then solely unsupervised autonomous networks. In accordance with the present invention, algorithmic module is used as a supervisor for the artificial neural network module. As a neural network module, the present invention preferably employs spiking neuronal networks, hereinafter referred to as SNN. Basic models of spiking neurons are reviewed by Wulfram Gerstner in Chapter 1 of "Pulsed Neural Network", edited by Wolfgang Maass and Christofer M. Bishop, The MIT Press, London England (2001). Computing methods for use with spiking neurons are presented by Wolfgang Maass in Chapter 2, of the same publication. SNN have often been implemented in VLSI which was also reflected in specific design schemes.

Adaptive Cardiac Resynchronisation Processor Elements

Figure 2A:
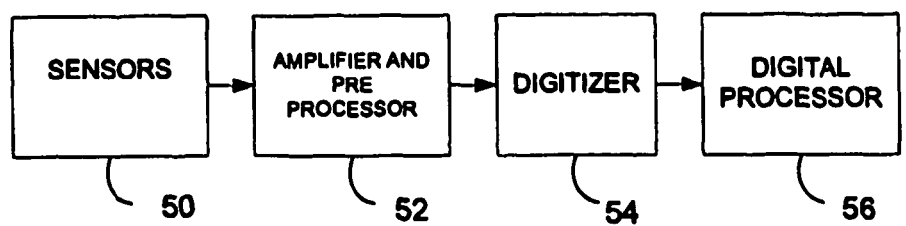
FIG. 2A is a schematic major component layout of an adaptive CRT device of the invention.
Figure 2B:
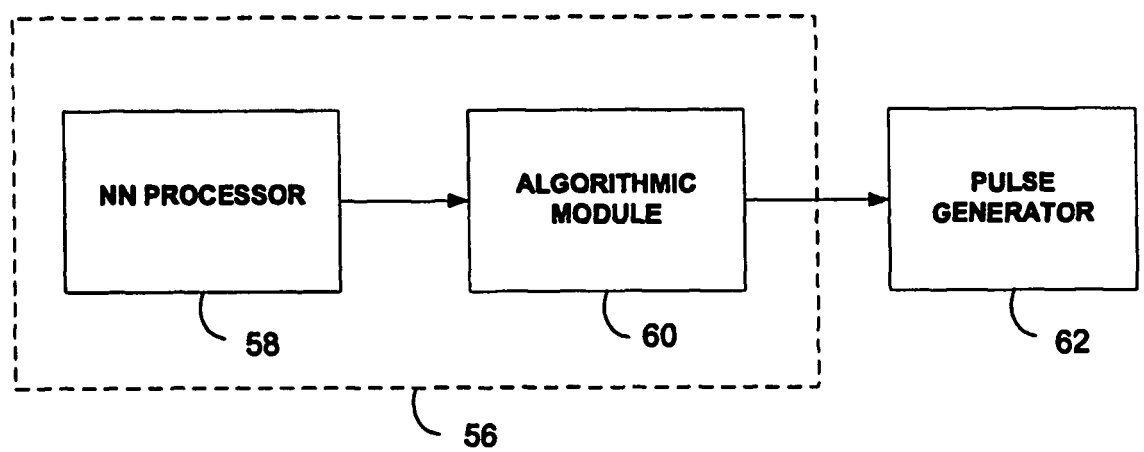
FIG. 2B is a schematic major processor output connections of the processing modules of the invention.

The adaptive CRT device aims at optimizing pacing parameters, AV delay and VV interval online, responding to the output of a hemodynamic sensor. The two parameters optimise the diastolic filling time, minimize mitral regurgitation (blood backflow) and ensure mechanical synchronization of both ventricles. A schematic block diagram describing the pacemaker/ICD device in accordance with a preferred embodiment of the invention is shown in FIGS. 2A and 2B. In FIG. 2A implanted or external sensors 50 monitor the electrical and hemodynamic activity of the patient's heart. The monitored signals are amplified and pre-processed by an analogue circuit 52 the output of which is digitized by A/D module 54 and processed by a digital processor 56. In the microprocessor 56 two sub-units are linked, as described schematically in FIG. 2B. An algorithmic module 58 performing an algorithmic process and neural network (NN) processor 60 performs a continuous adaptation process in connection with the algorithm, based on the changing circumstances detected by sensors 50. A pulse generator of the pacemaker \ICD device 62 is driven by the processor 56. In some embodiments of the invention processor 56 is implemented as a VLSI device.

In a preferred embodiment of the invention the NN module carries out spiking neural network (SNN) processes, whereas the algorithmic module performs as a master module. In a preferred embodiment of the invention, the master processor manages the pulse generator in order to deliver pacing or shock therapy, ensuring a safe operation of the system by an algorithm with a limiting high and low thresholds, limiting rates, limiting intervals and limiting amplitudes. The NN module or slave processor's task is to generate predictions for the optimal intervals for resynchronization of the left ventricle contraction with the right ventricle contraction at all heart rates, i.e replacing the fixed, programmed AV delay and VV interval parameters with dynamically changing AV and VV intervals, to be described below.

The Spiking Neural Network Module

In a preferred embodiment of the present invention a spiking neuron network (SNN) architecture is implemented in silicon for the following reasons:

1. SNN architectures specialize in continuous detection and classification of temporal sequences. The inputs to the SNN in the present invention are three intracardiac electrograms (IEGM) coming from the implanted electrodes in the right atria, right ventricle and outside of the left ventricle, and one or more inputs from hemodynamic sensors that are either implanted or non-invasive. All inputs described above deliver a continuous temporal signal that the SNN processors is required to process online.

2. SNN architecture has a massive parallel computation capability that allows a design of a processor with extremely low clock frequency such as 1-10 KHz and low power consumption.

3. SNN architecture performs local computation in each neuron and synapse module and stores data locally with no need to access external, on-chip or off-chip memory modules and hence allows to scale up to a massive parallel computation power with extremely low power dissipation.

A description of a preferred embodiment using specially designed SNN processor with novel learning rules is described below with reference to FIGS. 3-8.

Figure 3:
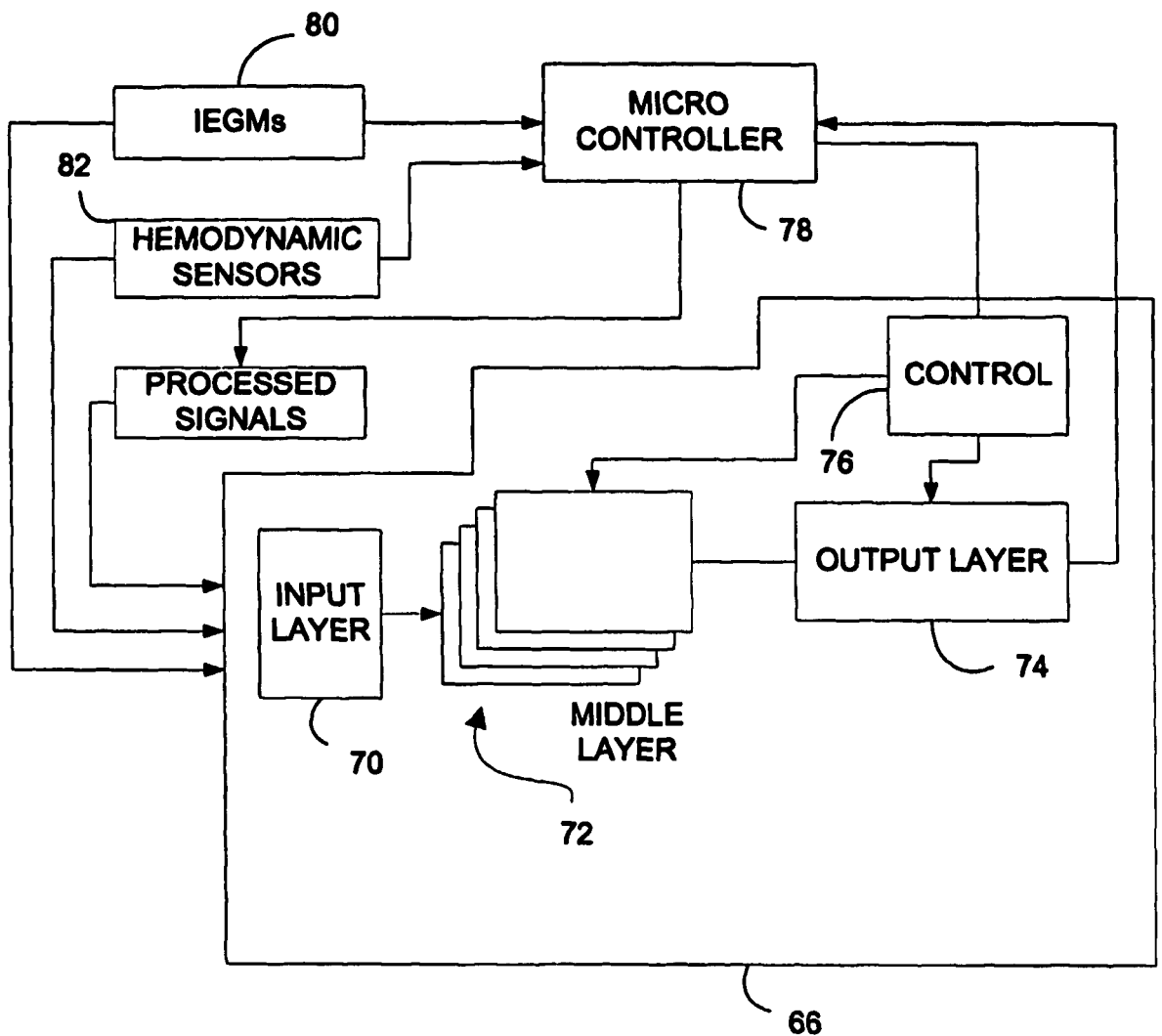
FIG. 3 is a neural network-micro controller architecture of a device of the invention.

FIG. 3 shows the spiking neural network (SNN) processor architecture. The SNN processor 66 has an input layer, 70, a middle layer, 72, and an output neuron layer 74. A control block, 76, performs calculations needed for the synaptic weights adaptation rules of the SNN processor in co-operation with the micro-controller module, 78, that are forwarded to the SNN middle and output layers. The input layer 70 receives inputs from the 3 implanted electrodes 80 from the heart chambers, data from hemodynamic sensors 82 such as impedance sensor from the right and left ventricles and pressure sensor. The three implanted electrodes are known collectively as intra-cardiac electrograms (IEGM) which deliver also pacing signals to the heart chambers. The micro-controller master can forward to the NN module processed data representing dynamic sensors such as the heart rate, a measure of the ventricles stroke volumes extracted from an impedance sensor, accelerometer sensor or a pressure sensor. The input layer 70 of the invention typically includes a pre-processing stage, a synchronizer decoder that excites an array of dynamic synapses in the middle layer.

The input layer synchronizer receives a trigger from the analog interface (an operational amplifier circuit) when a depolarization wave that initiates a new heart cycle sequence is detected by the atrial electrodes pair. Subsequent to the triggering, the synchronizer generates an excitation sequence to the dynamic synapse modules of the middle layer.

In the middle layer, the dynamic synapses perform the adaptation of the synaptic weight locally at the various learning schemes of the present invention. All the dynamic synapses of the middle layer are connected to the output layer. In the output layer there are two leaky integrate and fire (I&F) neurons modules and a feedback control unit that is connected to each leaky I&F neuron module. One I&F neuron affects the pacing of the right ventricle the second affects the pacing of the left ventricle. The two feedback control units manage the pacing registers that store the pacing interval values to be forwarded to the micro-controller, the algorithmic master module. The different modules of the SNN architecture and the management of the pacing registers in the feedback units will be described herein after.

Figure 4:
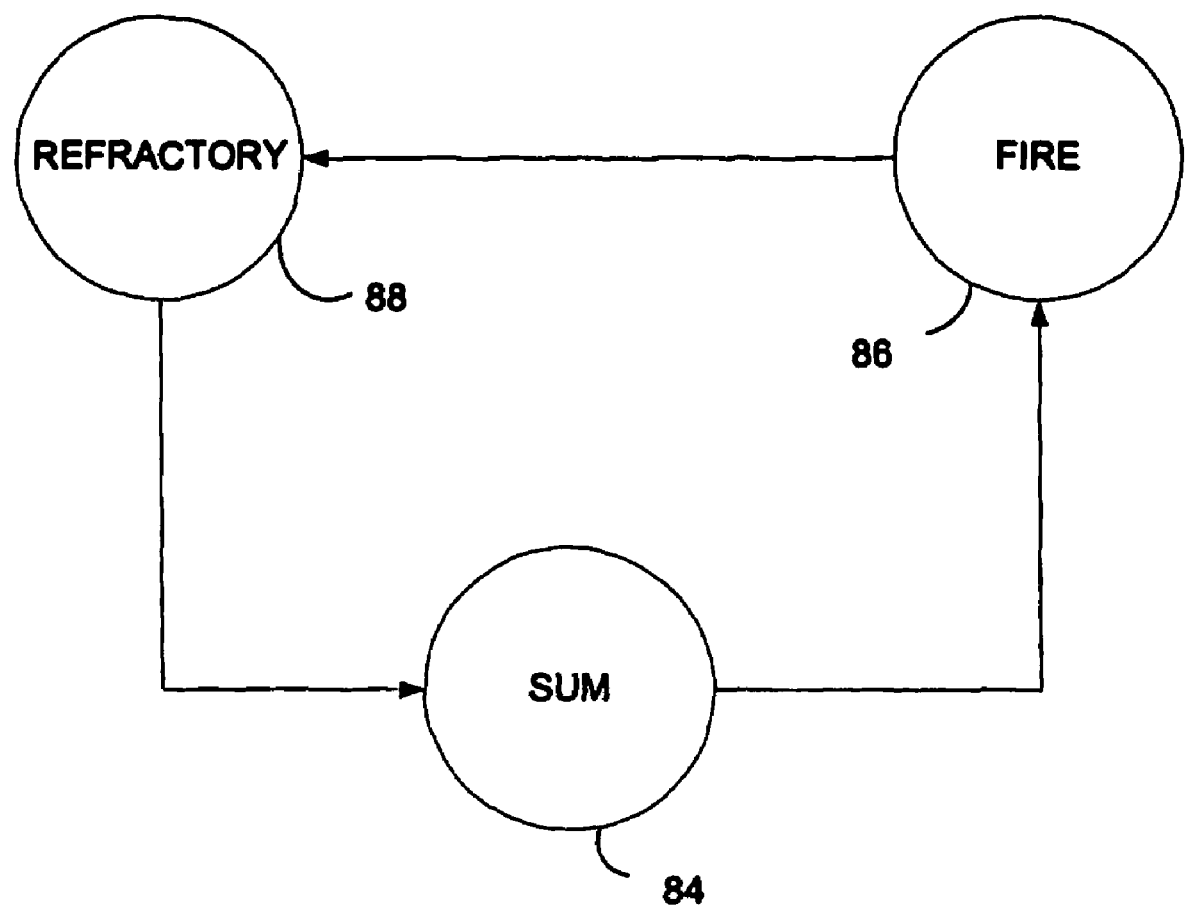
FIG. 4 is a state machine representation of a neuron of the learning module of the invention.

FIG. 4 shows an exemplary digital leaky I&F neuron implemented as a state machine, described hereinafter. The leaky I&F neuron is driven by excitatory and inhibitory synapses and has an internal membrane potential register (not shown). The neuron has three states, namely SUM state 84, FIRE state 86, and REFRACTORY state 88. In the SUM state, the neuron sums the input excitatory post-synaptic responses (EPSR) and inhibitory post-synaptic responses (IPSR) and accumulates the result in a membrane potential register. When the membrane potential reaches a threshold value, the state-machine makes a transition to the FIRE state, generating an output spike following which, the state-machine proceeds to the REFRACTORY state. The state machine waits for a fixed pre-defined period of time in the refractory state and returns to the SUM state. The I&F neuron model membrane potential has in addition a constant rate potential loss, i.e. leakage, that cause the membrane potential to decrease to zero value at a constant rate if no excitation occurs. The membrane potential leakage parameter is an important feature of the architecture of the SNN of the present invention since the leaky I&F neuron model enables processing temporal signals in real-time.

Figure 5A:
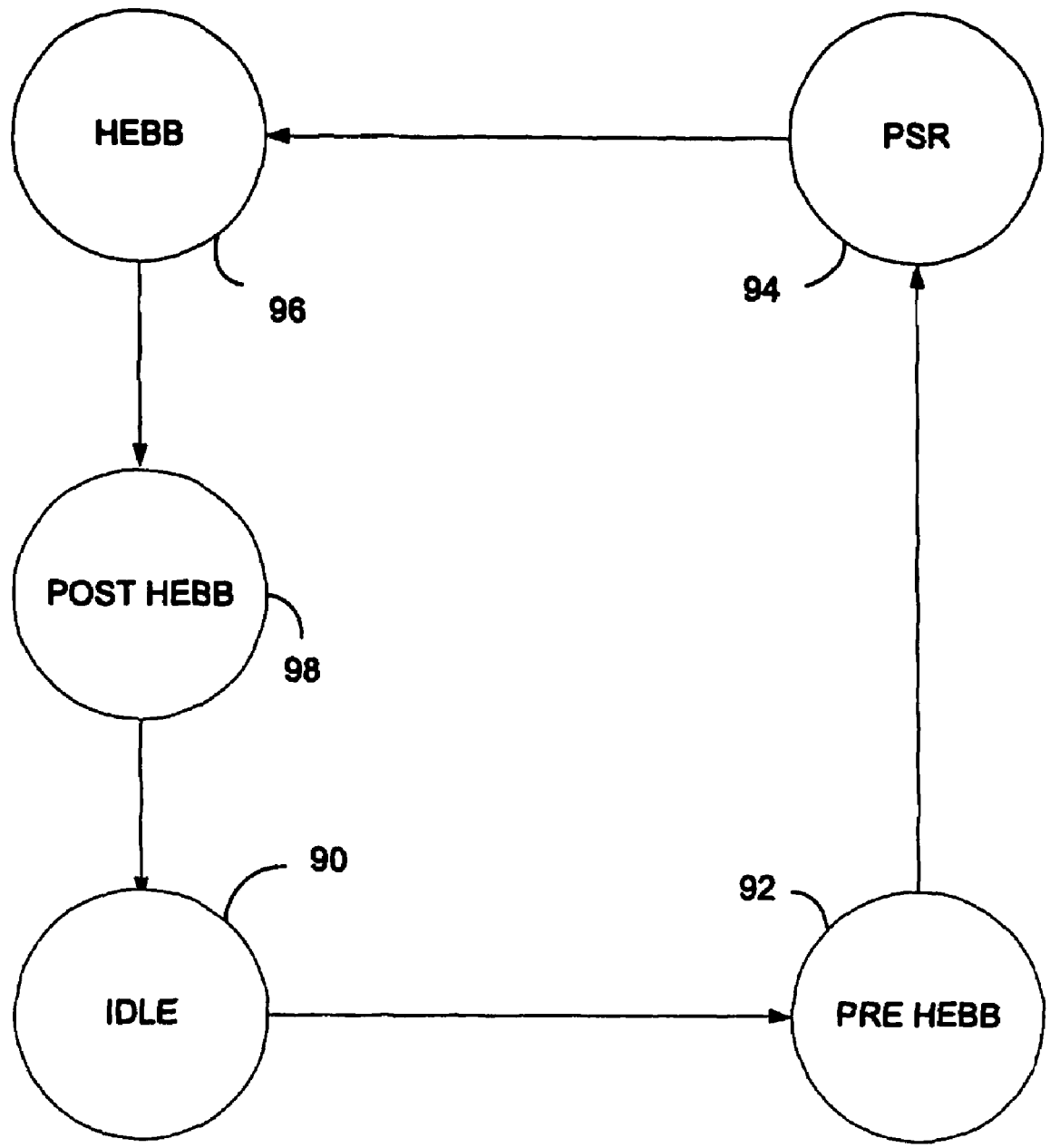
FIG. 5A is a synapse of the invention implemented as a state machine.

The synaptic module is also preferably implemented as a state machine as shown in FIG. 5A. The synapse has five states, namely IDLE, 90, PRE_HEBB 92, PSR 94, HEBB 96, and POST_HEBB 98. When a spike is received from a pre-synaptic neuron, a transition to the PRE_HEBB state occurs. After a pre-defined time delay, a transition to a post-synaptic response (PSR) state takes place and a PSR is emitted. The PSR is proportional to a stored synaptic weight, W, and it is a decaying function of time. After one clock period at the PSR state, the state machine enters the HEBB state. After a time delay the state machine transits to a POST_HEBB state and finally returns to the IDLE state.

Figure 5B:
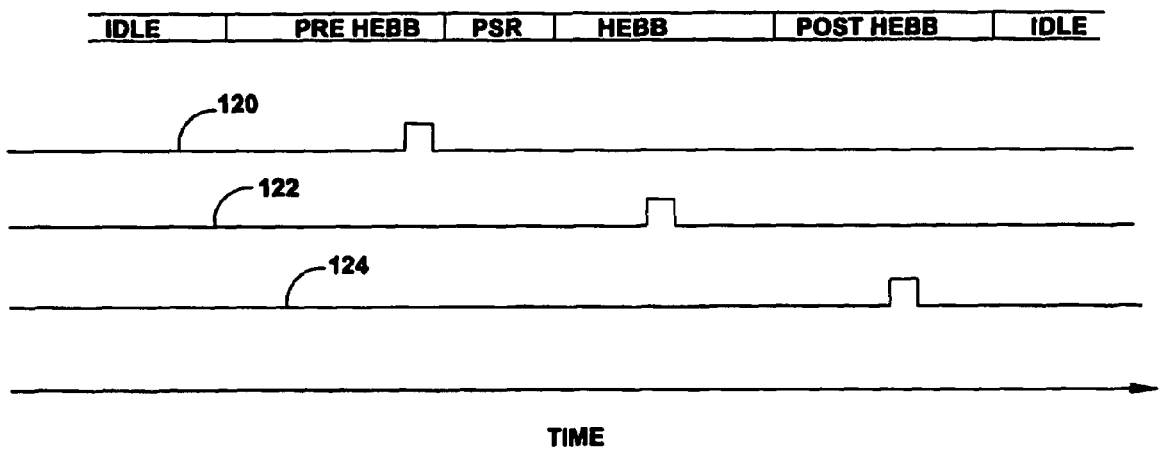
FIG. 5B shows a timing diagram of the dynamic synapse.

FIG. 5B shows the three Hebb sates described above, demonstrating output neuron spikes occurrences at three different states. In the first case designated by graph 120 the output neuron spike occurs at the pre-HEBB state. In the second case designated by graph 122 the post-spike occur at the HEBB state, and in the third case designated by graph 124, the spike occurs at the post-HEBB state. The identity of the state at which the spike has occurred is stored at the synapse every cardiac cycle and it affects the synaptic weights adaptation rules as described below.

The Synaptic Weights Adaptation Rules

The synaptic weights adaptation rules of the present invention are a combination of Hebb rule and a feedback control obtained by interaction with the environment through the hemodynamic sensors. The Hebb rule states that when a post-synaptic neuron fires after it was excited by a synaptic PSR, the synapse weight is strengthened. The environment is represented by the signals of the IEGM and by a hemodynamic sensors signal. In the present invention Hebb rule is implemented as described next. Of the five states described in FIG. 5A to which reference is again made, three are Hebbian, namely PRE_HEBB, HEBB and POST_HEBB. In FIG. 5B each synapse receiving an output neuron spike stores the corresponding state, i.e. PRE_HEBB, HEBB or POST_HEBB. The way these states enter the synaptic weights adaptation rules is explained below with reference to FIGS. 6A-B.

The Synaptic Weights Learning Rules of the Non Adaptive CRT Mode

As described above, a clinician programs the AV delay parameter and the VV interval parameter of the pacemaker as in prior art non-adaptive CRT devices, using parameters acceptable in the art, which subsequently generate a numerical baseline representation of the sensed hemodynamic performance using the programmed parameters above.

The present invention's SNN processor starts operating in a non-adaptive CRT mode pacing with the programmed intervals and the two I&F neurons of the output layer learning to fire at the programmed time stored. When the I&F neurons have learned to fire at the expected time, the processor switches to adaptive CRT mode in which the AV delay and VV intervals are changed dynamically. A numerical representation of the sensed hemodynamic performance is obtained in each cardiac cycle and the synaptic weights of the SNN processor are changed accordingly in order to deliver the AV delay and VV intervals that result in the best hemodynamic performance. Whenever the hemodynamic performance is lower than the recorded baseline value, a switch back to the non-adaptive CRT mode pacing with the initial AV delay and VV interval values programmed by the clinician occurs. It is expected that the SNN processor will work most of the time in the adaptive CRT mode facilitating optimal hemodynamic performance.

The synaptic weight learning rules applied during the non-adaptive CRT mode, takes into consideration two different items. One, the deviation of the spike of the output neuron from the programmed value in terms of time and two, the sampled Hebb states stored at each synapse, as shown in FIG. 5B to which reference is again made. The synaptic weights learning rule generates a shift of the firing time of the I&F neuron in the direction of the programmed time. The synaptic weights learning rule are as follows:—

When the output neuron spike occurs before the programmed time, synapses that were at PRE_HEBB state increment their weights, and synapses that were at HEBB or POST_HEBB states decrement their weight. When the output spike occurs after the programmed time, synapses that were at PRE_HEBB state decrement their weight, and synapses that were at HEBB or POST_HEBB states increment their weight. The synapse weight is limited to positive values and is also bound to be less then a pre-defined maximal value.

The non adaptive CRT learning rule is summarized in the equation below—

$$W_{ij} = W_{ij} + \eta * R_{ij} \quad \text{Equation 1}$$

Where:

i is the leaky I&F neuron index for the right and left ventricle neuron.

j is the synapse index for each spiking neuron.

η is a learning rate coefficient, (a typical value is 0.1).

$T_i$ is the firing time of the spiking neuron relative to the atrial depolarization wave.

$P_i$ is the programmed pacing interval which is also the supervised learning target time. In the non-adaptive CRT mode, the pacing interval $P_i$ can be changed only by the user, and not by the device learning schemes.

$R_{ij}$ is a function of the relative timing of the firing of the I&F neuron, $T_i$, and the target time, $P_i$, a hit or miss, which is determined by the absolute time difference, $|T_i-P_i|<15$ msec is a hit or otherwise a miss and a local Hebbian state that were described above. When the firing time of the I&F neuron occurs within a pre defined interval, Δ, after the synapse was excited the synapse state is stored as a Hebb state. When the firing time of the I&F neuron occurs between Δ and 2Δ after the synapse was excited the synapse state is stored as a post Hebb state. When the firing time of the I&F neuron occurs within an interval Δ before the synapse was excited the synapse state is stored as a pre Hebb state. With these definitions of local synaptic Hebb states, the $R_{ij}$ factor that appears in equation. 1 is shown in equation. 2 below Equation 2

$$R_{ij} = \begin{cases} +1 & \text{if } T_i > P_i, \text{ Miss, Post Hebb} \\ & \text{if } T_i > P_i, \text{ Hit, Hebb or Post Hebb} \\ & \text{if } T_i < P_i, \text{ Hit, Hebb} \\ & \text{if } T_i < P_i, \text{ Miss, Pre Hebb} \\ -1 & \text{if } T_i > P_i, \text{ Miss, Hebb or Pre Hebb} \\ & \text{if } T_i > P_i, \text{ Hit, Pre Heb} \\ & \text{if } T_i < P_i, \text{ Miss, Hebb or Post Hebb} \end{cases} \quad (2)$$

The Synaptic Weights Learning Rules in the Adaptive CRT Mode

Figure 6A:
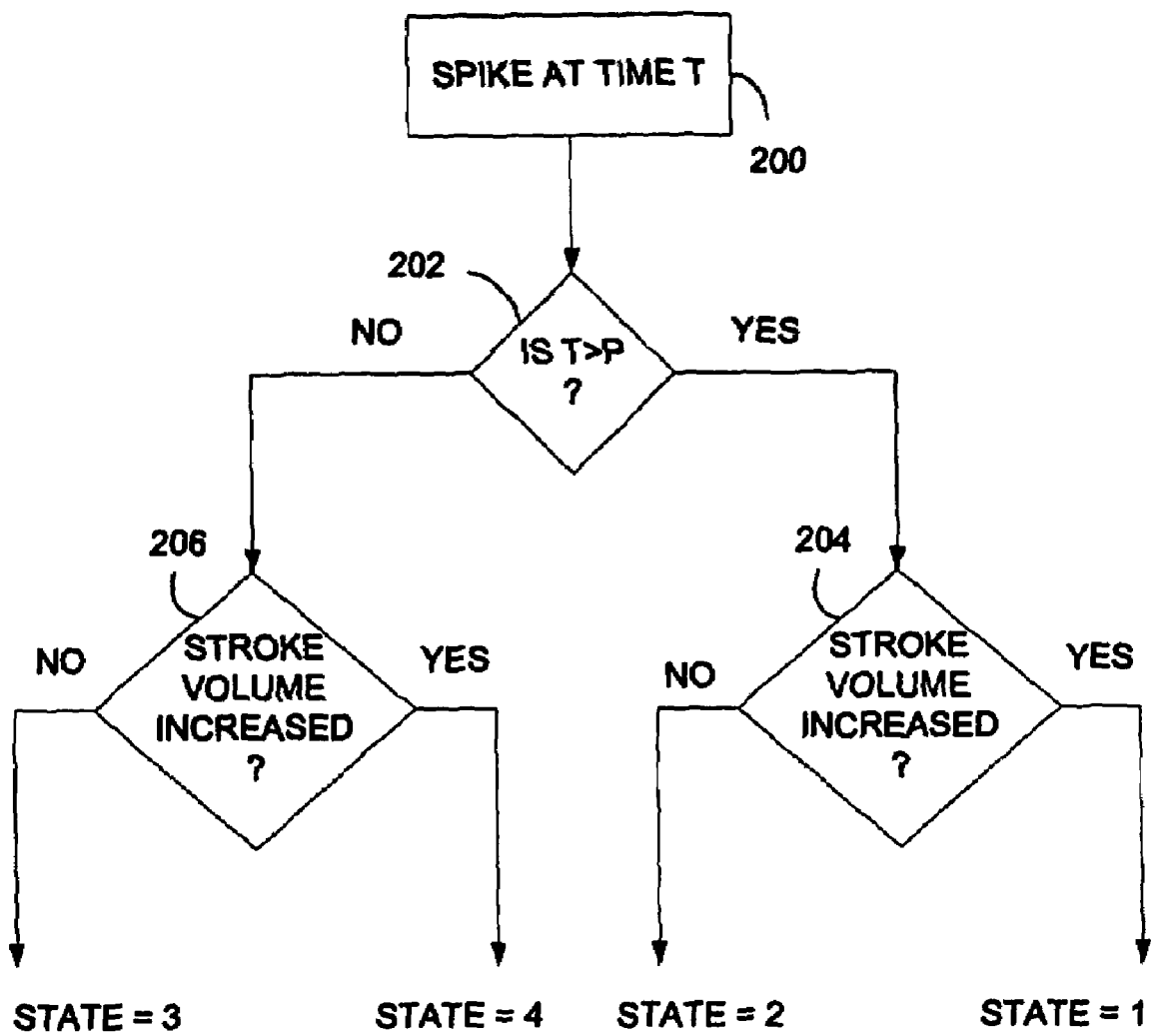
FIG. 6A is a synaptic weights adaptation rules of the present invention.
Figure 6B:
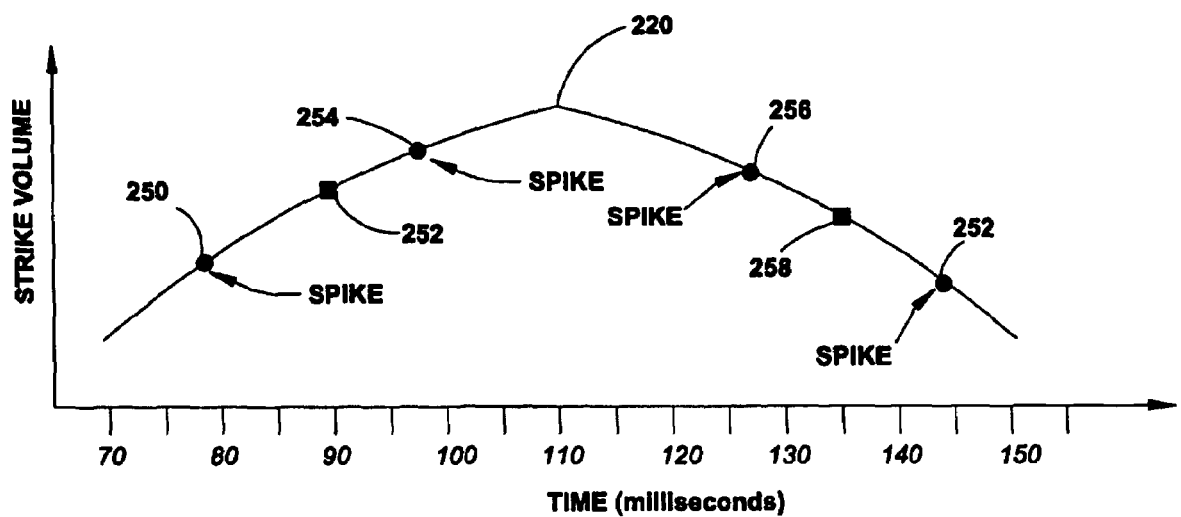
FIG. 6B is a flow chart for determining the state of a spike and the stored value at the pacing register with respect to the hemodynamic performance function of the heart.

Within the adaptive CRT mode the SNN processor modify its synaptic weights continuously interacting with the environment through the electric and hemodynamic sensors. FIG. 6A helps to explain the adaptive CRT mode synaptic weights learning rule. The output neuron fires at a time T measured from the sensed right atrial contraction every cardiac cycle, 200. The time T is compared, at step 202, with the time P stored at the pacing register of the output layer. If T>P the pacing register value is increased at step 204. Else, it is decreased at step 206. At the next cardiac cycle the pacemaker paces the heart with the updated values, stored at the pacing register. A numerical representation of the sensed hemodynamic performance is calculated with the updated pacing values and is compared, at steps 204 and 206, In one example the stroke volumes, SV, of the left or right ventricle is used as the hemodynamic performance criterion. Four possible states are defined by comparing the new stroke volumes with the previous stroke volumes. FIG. 6B. shows the adaptive CRT mode learning profile for the synaptic learning rules. The numerical representation of the hemodynamic performance has a maximal value 220 at some pacing time interval. The task performed in the adaptive CRT mode is to modify the synaptic weight such that the value stored at the pacing register is the value that maximizes the hemodynamic performance. After a spike occurs, a corresponding state is determined as relates to the stored pacing register value stored. Spike 250 relates to the recorded pacing register 252 stored, defining a state 3. Spike 254 accordingly, as relates to pacing register 252 defines a state 1, spike 256 as relates to pacing register 258 defines state 4, spike 260 relates to pacing register 258 defining state 2. After the state associated with a spike is determined, the synaptic weight modification value is calculated locally in each synapse and its value depends on the flow diagram state and on the Hebb state stored at each synapse as was shown in FIG. 5A to which reference is again made. When the state associated with a spike is classified as 1 or 3 as in FIG. 6B to which reference is again made, the firing intervals are to be increased. When the flow diagram state is classified as 2 or 4 the firing intervals are to be decreased. The synaptic weights are modified in each synapse separately in order to affect the firing time of the I&F neuron. Synapse in a PRE_HEBB state and is to increase its weight will cause the I&F neuron to increase firing intervals. A synapse in a POST_HEBB state and is to increase its weight will cause the I&F neuron to decrease firing intervals.

With the adaptive CRT mode the synaptic learning rule explained in details above using a flow diagrams of FIGS. 6A and 6B are summarized with Equations. 3 and 4 below.

$$W_{ij} = W_{ij} + \eta * R_{ij} \quad \text{Equation 3}$$

Equation 4, $$R_{ij} = \begin{cases} +1 & \text{if in state 1 or 3, PRE Hebb} \\ & \text{if in state 2 or 4, Hebb or Post Hebb} \\ -1 & \text{if in state 1 or 3, Hebb or POST Hebb} \\ & \text{if in state 2 or 4, Pre Hebb} \end{cases} \quad (4)$$

Where, $W_{ij}$, $\eta$ and $R_{ij}$ parameters were defined above.

Pacing Register Management

Within the feedback control unit of the output layer, dedicated registers store the dynamically changing AV delay and VV pacing interval. The pacing register modification scheme was shown in FIG. 6A in a flow diagram and the management of the pacing register is described as follows. When the I&F neuron firing time, T, is shorter than the stored pacing interval, P, the value is decremented. When the I&F neuron firing time, T is longer than the stored pacing interval, P the value is incremented. The increment/decrement step lasts typically 10 msecs, and the pacing interval physiologic range forced by the master controller lasts typically 50-200 msecs.

The synaptic weights learning rules described above, for both the non-adaptive and the adaptive CRT modes, occur simultaneously at each output neuron, in which an optimized function is defined for each output neuron. The optimized function is for example the hemodynamic performance such as the stroke volumes of each ventricle extracted from the hemodynamic sensors. The implanted hemodynamic sensors used with the present invention can be a ventricle blood impedance sensor (for example Bio-Impedance Sensor, ELA Medical, France), an accelerometer sensor (for example, PEA® sensor, Sorin Group, Italy), a pressure sensor (for example the Chronicle® device right ventricular pressure sensor, Medtronic Inc, USA), a QT interval sensor (for example, Ishikawa et al, PACE Vol. 25, No. 2, 195-200, 2002)

External Adaptive CRT Device

Another preferred embodiment of the present invention is an externally adaptive CRT device for diagnostics and cardiac rehabilitation. The external adaptive CRT device receives IEGMs and hemodynamic data using a communications channel, preferably a neural network module, or other learning modules, processes the data in the external device. In this case the external adaptive CRT device is not implanted in the patient's body, and it transmits to a biventricular pacemaker or defibrillator implanted in the patient's body the optimal pacing parameters, AV delay and VV interval, to the pacemaker on-line. The diagnostics and rehabilitation procedure can be supervised by a clinician at a cardiac rehabilitation centre. The system of the invention, facilitates diagnostics and rehabilitation procedure of some form to be carried out at the patient environment (home, office etc) without the supervision of a clinician. The hemodynamic sensor used is an implanted sensor such as a ventricle blood impedance sensor (for example, Bio-Impedance Sensor, ELA Medical, France), accelerometer sensor (for example, PEA sensor, Sorin Group, Italy), a pressure sensor (for example the Chronicle® device right ventricular pressure sensor, Medtronic Inc, USA), a QT interval sensor (for example, Ishikawa et al, PACE Vol. 25, No. 2, 195-200, 2002) or a non-invasive hemodynamic sensor such as impedance sensors (such as BioZ® sensor of Cardio-Dynamics Inc. San Diego, Calif., USA) or an echocardiograph. In the case of an echocardiograph, the images of the wall motion in one example are to be interpreted numerically to hemodynamic performance function, to be further used for optimisation by an external adaptive CRT device in accordance with the present invention.

Benefits of the Adaptive CRT Device

Adaptive CRT Device Cardiac Rehabilitation Capability

The system of the present invention uses the information derived from the hemodynamic sensor in two complementary ways. One, the specific hemodynamic condition correlates with a specific hemodynamic performance representation, and two, a classification of the heart's condition is performed. For each heart condition, the optimal AV delay and VV interval are learned and updated continuously. Hence, the present invention adaptive CRT device can improve gradually the patient hemodynamic performance and hence the adaptive CRT device of the invention allows for a gradual cardiac rehabilitation. This work scheme constitutes a potential clinical improvement in hemodynamic performance such as the cardiac output and left ventricular function as reported recently by D. Odonnell et al, cited above.

Consistent Delivery of CRT

Atrial event tracking is an important issue in cardiac timing cycles in general which has also strong implication on CRT devices, as described in "Device Therapy for Congestive Heart Failure" by K. Ellenbogen et al, Elsevier Inc. (USA), 2004. In existing CRT devices, CRT is not delivered consistently due to loss of atrial tracking for hours and even for days as can be seen by pacemaker diagnostics in patients' follow-ups. Loss of atrial tracking occurs due to several reasons, for example, surpassing the programmed maximal tracking rate (MTR) during exercise. The MTR is especially important for CRT patients since when they start to exercise their cardiac output is too low for their metabolic demand, and therefore their heart rate starts increasing in order to increase cardiac output. When the patient heart rate reaches the programmed MTR (typically 120-150 BPM), the implanted pacemaker stops delivery of CRT pacing and the cardiac output drops. The adaptive CRT device of the present invention, can overcome the problem of loss of CRT delivery beyond the MTR as described above.

Figure 7:
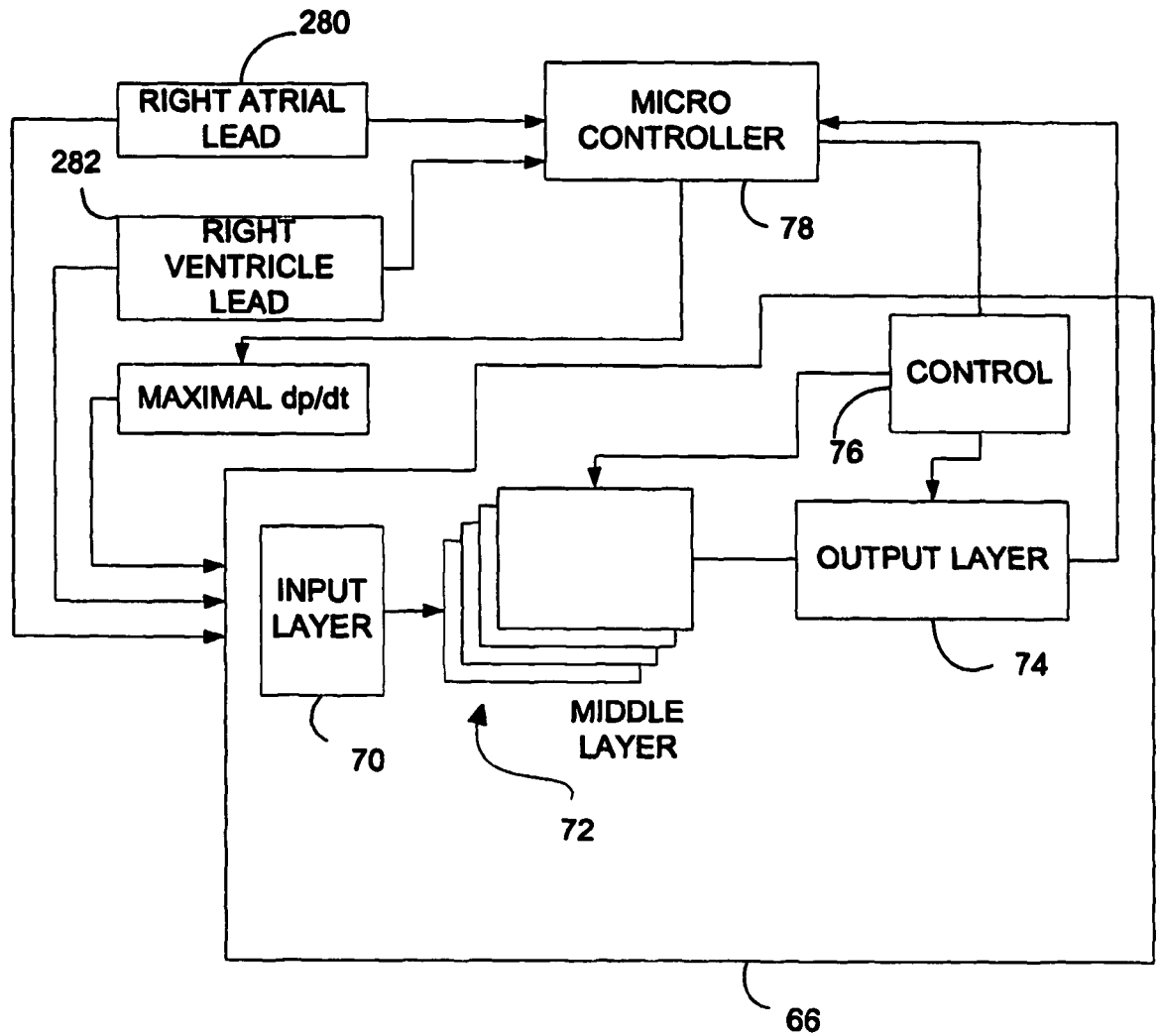
FIG. 7 is a block diagram of an adaptive rate responsive pacemaker using right ventricular and right atrial leads as sensors and pacing the right atria.

The SNN processor can learn to predict the next atrial event relative to the preceding ventricular event using the hemodynamic sensor signal. In FIG. 7 a block diagram is shown representing an adaptive CRT device that learns to predict the next atrial event and hence can also be used for a rate responsive pacemaker based on the present invention as explained further below. The sensors used are right atrial lead 280, right ventricle lead 282, and a ventricular pressure sensor or impedance, not shown. Beyond the MTR the adaptive CRT device of the present invention can replace the sensed atrial event using with the neural network processor prediction instead, thereby providing for a continuous delivery of CRT, i.e. pacing the right and left ventricles with the optimal AV delay and VV interval according to a hemodynamic sensors.

Adaptive Rate Response

Prediction of the desired optimal rate response to the physiological demand in response to all the patient conditions is a complex task needed for bradycardia patients with a sick sinus node. The currently used motion sensors do not respond to physiological/mental stress or anxiety which are not accompanied by an increase in the upper body motion. On the other hand, motion sensors respond to non-physiological events such as a bus ride, a plane take-off, operating a household drill, and other events external to the body and metabolic sensors are too slow to respond.

An adaptive rate response pacemaker in accordance with the present invention, senses the ventricle contraction and paces the right atria, with the same SNN architecture of the present invention for adaptive CRT device presented above (using only one output neuron). The SNN processor predicts the optimal timing for pacing the right atria such that the stroke volume, extracted from a pressure sensor as maximal dp/dt or as maximal amplitude difference with a ventricular blood impedance sensor between the diastole and systole cycle, is optimized in all heart conditions. In FIG. 7 a block diagram is shown representing an adaptive rate responsive pacemaker based on the present invention. The advantage of the adaptive rate response pacemaker of the present invention is in the online, continuous adaptation to the patient hemodynamic needs with an algorithm that maximizes the hemodynamic performance.

Adaptive Capture Management

As discussed in U.S. Pat. No. 6,456,881, pacemakers with auto-capture functions preserve energy and hence have a longer battery life. They also have the advantage of causing less patient discomfort due to an excessive heart stimulation. However, compiling the auto-capture function is a complex task due to the high variability of the heart electrical activity signals, and in particular, to the so called "fusion" phenomenon, exhibiting overlaps in time of the evoked response and internal beat. For CRT devices, capture management is even more important issue, since it is harder to capture the left ventricle comparing to the right ventricle. Usually, a higher pulse energy is used for the left ventricle and still it is not guaranteed that the left ventricle is consistently captured. Since with the adaptive learning the pacing interval delivered to the ventricles are not constant we can predict the time difference between the evoked response in the current cardiac cycle and the evoked response of the next cardiac cycle. If the sensed ventricular event matches the timing of the prediction, it is defined as an evoked response and capture is verified. If the ventricular event timing does not match the predicted, the beat is an intrinsic ventricular beat. The ability to differentiate between evoked response beat from intrinsic beat using the adaptive CRT device algorithm can be used to manage the pulse energy in order to save battery energy while ensuring capture.

Adaptive AV Delay for Dual Chamber Pacemakers and ICDs

AV delay optimization of dual chamber pacemakers and defibrillators are as important clinically as the AV delay optimization of CRT devices. Dual chamber devices use one atrial electrode and one ventricular electrode, and a ventricular pacing occurs after the pre-programmed AV delay measured from a sensed or paced atrial event ends. The natural AV delay in a healthy heart depends on heart rate and on stress conditions and vary from patient to patient and during patient's daily activities and a fixed pre-programmed AV delay is less then optimal. The present invention for optimising adaptive CRT (and a CRT device combined with a defibrillator known as a CRT-D) devices optimize both the AV delay and the VV interval lends itself easily to implementation as an adaptive dual chamber devices with dynamic optimization of the AV delay according to implantable hemodynamic sensor and using a neural network processor in the same manner. Hence the same neural network architecture implementation, learning rules, clinical benefits and low power consumption will be seen also with an adaptive dual chamber pacemaker or defibrillator (ICD) which are another preferred embodiment of the present invention.

Closed Loop Adaptive Medical Devices

Other closed loop medical devices delivering physiologically active signals can benefit from the combined system of a learning module and deterministic module that serve also as a supervisor for the learning module as presented in this invention. The architecture guarantees safe operation and at the same time allow adaptive, sensitive to the patient system. It is expected to improve performance of various closed loop, feed back controlled therapeutic medical device such as an implanted, closed loop Insulin pump, a controlled drug delivery systems, brain stimulation devices for patients with Parkinson disease, etc. Hence, the cardiac pacemakers and ICD's are only one implementation of the invention.

The invention claimed is:

1. An adaptive feed-back controlled cardiac resynchronisation therapy system capable of dynamic AV delay and VV interval pacing related to changes in the data received from at least one hemodynamic sensor continuously monitoring a hemodynamic performance, said system comprising:
  a learning neural network module, for receiving and processing information of said at least one sensor and for learning at least one aspect of said hemodynamic performance body;
  a deterministic algorithmic module, receiving parameters of said resynchronisation therapy from said neural network module, and
  a therapeutic delivery means, for delivering said resynchronisation therapy, said therapeutic delivery means is connected to said deterministic algorithmic module and operated by it;
wherein in a non-adaptive operation mode of said system, said deterministic algorithmic module is used for implementing a supervised learning scheme of said learning neural network module, and wherein said resynchronisation therapy is delivered according to parameters pre-programmed into said deterministic algorithmic module; and
wherein in an adaptive operation mode of said system, said learning neural network module is used for dynamically changing the parameters of said resynchronisation therapy according to the information received from said at least one hemodynamic sensor, and wherein said resynchronisation therapy is delivered according to the parameters provided by said learning neural network module.

2. A system according to claim 1 wherein said modules and therapeutic delivery means are implanted, delivering biventricular pacing with adaptive AV delay and VV interval, modified continuously with correlation to the hemodynamic performance of the heart.

3. A system according to claim 1 wherein said neural network module employs a spiking neuron network architecture.

4. A system according to claim 1 wherein said neural network module employs a spiking neuron network architecture implemented as a silicon processor operating with extremely low clock frequency.

5. A system according to claim 1 wherein said neural networks module is external.

6. A system according to claim 1 wherein said at least one sensor is a non invasive sensor.

7. A system according to claim 1 wherein said therapeutic delivery system is connected to said learning neural network module via a wireless communications link.

8. A system according to claim 1 wherein said therapeutic delivery means is at least one selected from the group consisting of a biventricular pacemaker and a defibrillator, a biventricular pacemaker and a CRT-D device or any combination thereof.

9. A method for adaptive biventricular pacing control comprising the steps of:
   obtaining continuous signal from at least one sensor monitoring physiological parameter of said patient;
   processing said continuous signal by an algorithmic processing module and a learning module and wherein said learning modules carries out adaptive learning in connection with said at least one sensor is first supervised by applying an accepted set of parameters, and
   delivering a physiological signal by a delivery module in response to said processed signal, wherein said regulation either relates to said algorithmic process or to said learning process,
   programming initial AV (atriaventricular) delay parameter and VV (interventricular delay) interval parameter of an algorithmic module;
   providing pacing in a non-adaptive CRT mode wherein an algorithmic deterministic module controls the delivery of pulses, and wherein pacing is provided according to said parameters,
   switching to an adaptive CRT mode wherein said AV delay and VV interval change dynamically in order to achieve optimal hemodynamic performance, and wherein said adaptive mode is limited to perform above a low limit of hemodynamic performance, and
   switching back to the non adaptive CRT mode whenever the hemodynamic performance is below a low limit of hemodynamic performance or a sensor failure or any other system failure is detected.

10. A method for adaptive dual chamber control, comprising the steps of:
   performing the steps 1 to 3 as set forth in claim 9; wherein said delivery module is any selected from the group consisting of: a dual chamber pacemaker and dual chamber defibrillator (ICD);
   programming initial AV (atriaventricular) delay parameter of an algorithmic module;
   operating in non-adaptive mode wherein an algorithmic deterministic module for controlling delivery of pulses, wherein pacing is carried out according to said parameter and wherein learning operation with said parameters takes place;
   switching to adaptive mode whereby said AV delay changes dynamically in order to achieve optimal hemodynamic performance, and wherein said adaptive mode is limited to perform above a predefined low limit of hemodynamic performance, and
   switching back to non adaptive mode whenever the hemodynamic performance is lower than a low limit of hemodynamic performance or a sensor fails or any other system failure is detected.

11. A method for adaptive biventricular pacing control as in claim 9 or a method for adaptive dual chamber pacing control as in claim 10, wherein said sensor information relates to at least one sensor selected from the group consisting of: a ventricular pressure sensor, a ventricular blood impedance sensor, a ventricular wall motion accelerometer sensor and a QT interval sensor.

12. A method for adaptive biventricular pacing control as in claim 11, used for ventricular pacing beyond the maximal tracking rate (MTR) limit, wherein the neural network processor is trained to predict the atrial event timing relative to the preceding ventricular event using the hemodynamic sensor signal that reflects ventricular contraction and where the predicted atrial event replace the sensed atrial event when the MTR limit is reached.

13. A method for adaptive biventricular pacing control and a rate responsive atrial pacing as in claim 11, wherein said patients are bradycardia patients, and wherein the neural network processor predicts the optimal atrial event timing relative to the preceding ventricular event using the hemodynamic sensor signal that reflects ventricular contraction and where a stroke volume is optimized.

14. A method for adaptive biventricular pacing control and for ventricular capture management as in claim 11, wherein the changes in the evoked response timing are correlated with the variation in pacing intervals timings and hence a capture is verified reliably and an intrinsic ventricular beat can be discriminated from a ventricular evoked response.

15. A method for adaptive biventricular pacing control as in claim 9 or a method for adaptive dual chamber pacing control as in claim 10, wherein said learning module is a neural network module.

16. A method for adaptive biventricular pacing control and a rate responsive atrial pacing as in claim 15, wherein said patients are bradycardia patients, and wherein the neural network processor predicts the optimal atrial event timing relative to the preceding ventricular event using the hemodynamic sensor signal that reflects ventricular contraction and where a stroke volume is optimized.

17. A method for adaptive biventricular pacing control and for ventricular capture management as in claim 15, wherein the changes in the evoked response timing are correlated with the variation in pacing intervals timings and hence a capture is verified reliably and an intrinsic ventricular beat can be discriminated from a ventricular evoked response.

18. A method for adaptive biventricular pacing control as in claim 15, used for ventricular pacing beyond the maximal tracking rate (MTR) limit, wherein the neural network processor is trained to predict the atrial event timing relative to the preceding ventricular event using the hemodynamic sensor signal that reflects ventricular contraction and where the predicted atrial event replace the sensed atrial event when the MTR limit is reached.

19. A method for adaptive biventricular pacing control as in claim 9 or a method for adaptive dual chamber pacing control as in claim 10, wherein a synaptic weight learning rule is Hebbian.

20. A method for adaptive biventricular pacing control as in claim 9 or a method for adaptive dual chamber pacing control as in claim 10, wherein said learning module is a neural network module; wherein said neural network module employs a spiking neuron network architecture implemented as a silicon processor operating with extremely low clock frequency and hence dissipate extremely low battery power.

* * * * *